(12) United States Patent
Fischer et al.

(10) Patent No.: US 8,149,505 B2
(45) Date of Patent: Apr. 3, 2012

(54) LASER SCANNER DEVICE WITH LIMITED TEST PART ACCESSIBILITY

(75) Inventors: Frank Fischer, Salzburg (AT); Harald Gebetsroither, Grödig (AT); Andreas Gfrörer, Königsdorf (DE); Andreas Schenk, Fürstenbrumm (AT)

(73) Assignee: Tecan Trading AG, Mannedorf (CH)

( * ) Notice: Subject to any disclaimer, the term of this patent is extended or adjusted under 35 U.S.C. 154(b) by 903 days.

(21) Appl. No.: 12/191,137

(22) Filed: Aug. 13, 2008

(65) Prior Publication Data

US 2009/0065709 A1  Mar. 12, 2009

(30) Foreign Application Priority Data

Aug. 17, 2007  (CH) ........................................ 1301/07

(51) Int. Cl.
*G02B 21/26* (2006.01)
(52) U.S. Cl. ........... 359/391; 359/392; 356/244; 436/46
(58) Field of Classification Search .................. None
See application file for complete search history.

(56) References Cited

U.S. PATENT DOCUMENTS

| | | | |
|---|---|---|---|
| 4,367,915 A | 1/1983 | Georges | |
| 4,741,043 A * | 4/1988 | Bacus | ........................... 382/129 |
| 5,690,892 A | 11/1997 | Babler et al. | |
| 5,694,212 A * | 12/1997 | Weissman | .................. 356/237.1 |
| 6,794,424 B2 | 9/2004 | Holcomb et al. | |
| 6,800,249 B2 * | 10/2004 | de la Torre-Bueno | .......... 422/63 |
| 6,847,481 B1 | 1/2005 | Ludl et al. | |
| 7,205,045 B2 | 4/2007 | Holcomb et al. | |
| 2003/0015668 A1 | 1/2003 | Montagu | |

FOREIGN PATENT DOCUMENTS

| | | |
|---|---|---|
| GB | 1593064 A | 7/1981 |
| GB | 2184321 | 6/1987 |

* cited by examiner

*Primary Examiner* — Arnel C Lavarias
(74) *Attorney, Agent, or Firm* — Notaro, Michalos & Zaccaria P.C.

(57) ABSTRACT

A laser scanner device (1) for imaging and/or measuring fluorescent samples located on slides and treated using fluorescent pigments includes a sample table (2) defining a sample plane (49) and a motorized transport device (3) for moving a slide from a storage unit (4) to the sample table (2) and back. The storage unit (4) includes one sample part (7) for sample slides (8) and one test part (9) for test slides (10), each having at least one depository (6) and being accessible during the operation of the laser scanner device (1) for the transport device (3). The test part (9) is implemented separately from the sample part (7) and as a test part magazine (9') that is permanently connected to the laser scanner device (1) for one or more test slides (10).

6 Claims, 3 Drawing Sheets

LASER SCANNER DEVICE WITH LIMITED TEST PART ACCESSIBILITY

RELATED PATENT APPLICATIONS

This patent application claims priority of the Swiss patent application No. 2007 01301/07 filed on Aug. 17, 2008, the whole content of which is incorporated herein by explicit reference for all intents and purposes.

RELATED FIELD OF TECHNOLOGY AND PRIOR ART

The invention relates to a laser scanner device for imaging fluorescent samples located on slides and treated using fluorescent pigments.

Conventional optical scanning microscopes have been used for some time for imaging fluorescent samples located on slides. Confocal optical scanning microscopes are also being used more and more frequently because of the improved resolution. Such a microscope is known, for example, from GB 2 184 321 A. Many of the commercially available microscopes have beam splitters or filters for dividing the light emitted by the sample into beams having different wavelength ranges. Two fluorescent pigments may thus be used and their emission may be measured using two different detectors.

If such scanning microscopes or optical scanners are used, it is typical to test the physical properties of the device at least sporadically. For example, intensity and sensitivity tests are performed on fluorescent test objects, as is known, for example, from the patents U.S. Pat. No. 6,794,424 B2 and U.S. Pat. No. 7,205,045 B2. However, a suitable test object must be used in the device in each case for performing such tests, which may cause damage or contamination of the test objects. In addition, incorrectly- or wrongly-used test objects do not provide suitable results usable for calibrating the sensitive devices. The performance of the tests is also quite complicated and may additionally be put into question by gradual bleaching of the fluorescent test objects.

OBJECT AND SUMMARY OF THE PRESENT INVENTION

The object of the present invention is to suggest an alternative laser scanner device for imaging fluorescent samples located on slides and treated using fluorescent pigments, using which the required calibrations and tests may be performed more reliably.

This object is achieved by a laser scanner device according to the features as herein disclosed. The laser scanner device according to the invention for imaging and/or measuring fluorescent samples located on slides and treated using fluorescent pigments comprises a sample table defining a sample plane and a motorized transport device for moving a slide from a storage unit to the sample table and back, the storage unit comprising one sample part for sample slides and one test part for test slides, which each have at least one depository and are accessible to the transport device during the operation of the laser scanner device. The laser scanner device according to the invention is characterized in that the test part is implemented separately from the sample part and as a test part magazine, permanently connected to the laser scanner device, for one or more test slides, whereby a test slide stored in the test part is not manually accessible to an operator in the operating state of the laser scanner device.

Additional preferred features and features according to the invention result from the following specification and from the dependent claims.

Advantages of the laser scanner device according to the invention comprise:

One or more test objects may be permanently stored in the device, which is thus ready at any time to perform intensity and sensitivity tests, for example, crosstalk, resolution, dynamics, laser noise, and laser intensity measurements, and filter blocking and filter transmission tests, as well as for checking the adjustment of optical components, the geometric image parameters, and the image orientation.

An automatic calibration cycle is provided, the calibration occurring at predefined intervals which are only determined by the device and may not be influenced by the typical users.

Although sample magazines replaceable by arbitrary operators may be used in the device, the test objects are only accessible to these operators in operation of the device and thus not manually.

Normally, only one service technician is capable of exchanging and/or replacing test objects in the device.

The same mechanism may be used for bringing a sample slide and also bringing a test slide to the sample table and/or for removing each of these slides from the sample table.

The test objects stored in the device are protected as much as possible from the influences of the environment and are subject to practically no aging.

The use of essentially light-stable test objects allows more consistent results to be achieved.

BRIEF INTRODUCTION OF THE DRAWINGS

The laser scanner device according to the invention will now be explained on the basis of schematic drawings, which are not to restrict the scope of the present invention and represent examples of especially preferred embodiments. In the figures:

FIG. 3 shows vertical views of the slide magazines having open test object magazine, FIG. 3A showing the insertion side of the two slide magazines in a frontal view seen from the object table, and FIG. 3B showing the two slide magazines in vertical section looking toward the object table;

DETAILED DESCRIPTION OF THE INVENTION

Figure 1:
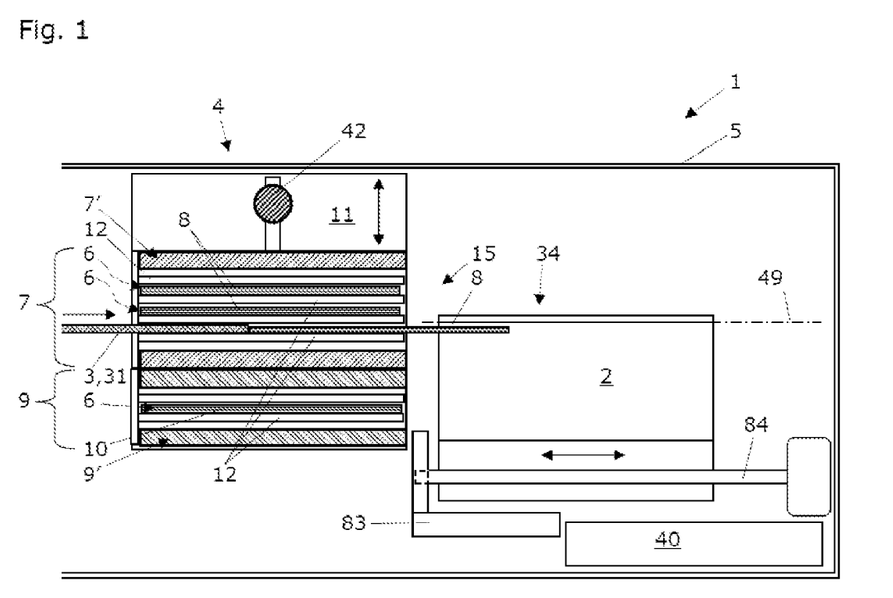
FIG. 1 shows a vertical partial section through two slide magazines and an object table placed in front of them during transfer of a slide from the sample magazine to the object table.

FIG. 1 shows a vertical partial section through two slide magazines and an object table placed in front of them during transfer of a slide from the sample magazine to the object table. These two slide magazines belong to a laser scanner device 1 according to the invention for imaging and/or measuring fluorescent samples located on the slides and treated using fluorescent pigments. This laser scanner device comprises a sample table 2 defining a sample plane 49, and a motorized transport device 3 for moving a slide from a storage unit 4 to the sample table 2 and back. The storage unit 4 comprises one sample part 7 for sample slides 8 and one test part 9 for test slides 10, each having at least one depository 6 and accessible to the transport device 3 during operation of the laser scanner device 1. In this laser scanner device according to the invention, the test part 9 is separated from the sample part 7 and implemented as a test part magazine 9', permanently connected to the laser scanner device 1, for one or more test slides 10. A test slide 10 stored in the test part 9 is thus not manually accessible to an operator in the operating state of the laser scanner device 1. This has the advantage that a suitable test slide may be provided at any time without such a test slide 10 being contaminated or even damaged by improper manipulations by operators. The test part magazine 9' shown here comprises an open insertion side 15.

In the embodiment shown here, the sample part 7 is situated axially above the test part 9 and the test part 9 of the storage unit 4 is permanently connected to a positioning plate 11 of the storage unit 4 which is movable in relation to the sample table 2 of the laser scanner device 1. The positioning plate 11 of the storage unit 4 is displaceable essentially perpendicularly in relation to the sample plane 49 of the sample table 2. An arbitrary slide 8,10 may thus be brought to the level of the sample plane 49 defined by the sample table 2 and provided for linear transport onto the sample table 2.

Notwithstanding this illustration in FIG. 1, the positioning plate may also be fixed and thus provide a stationary connection between the laser scanner device 1 and the test part magazine 9'. In such a case, the sample table 2 must be moved in relation to the test part magazine 9' if a linear transport of an arbitrary slide 8,10 from a sample part magazine 7' or a test part magazine 9' onto the sample table 2 is to occur. A positioning plate 11 may also be dispensed with entirely and the test part magazine 9' may be fastened anywhere on the laser scanner device 1 in such a way that a test slide 10 stored in the test part 9 is not manually accessible to an operator in the operating state of the laser scanner device 1.

Further alternatives (not shown) comprise a movement of a test slide 10 already located in the sample plane 49 of the sample table 2 in this sample plane 49 in relation to a stationary sample table 2, a movement of the sample table 2 in this sample plane 49 in relation to a stationary test part magazine 9', or a mutual movement of sample table 2 and test part magazine 9'. In all of these cases, a linear transport of an arbitrary slide 8,10 from a sample part magazine 7' or a test part magazine 9' onto the sample table 2 is made possible. In addition, using a robot is conceivable, which removes a slide 8,10 from one of the magazines 7',9' and places it on the sample table 2; in this case, the magazines 7',9' and the sample table 2 may assume a practically arbitrary position to one another.

However, it is preferable for the sample plane 49 of the sample table 2 to be situated essentially horizontally, the sample table 2 supporting a slide 8,10 above it. The sample table 2 may also be situated overhead, however, so that the slide 8,10 used is situated below the sample table. Any arbitrary other location of the sample plane 49 in space is also fundamentally conceivable, but is less preferable.

The laser scanner device 1 according to the first embodiment shown in FIG. 1 preferably comprises a housing 5, the sample part 7 being implemented as a magazine 7' for a plurality of sample slides 8 insertable from the outside into the housing 5 of the laser scanner device 1. The sample part 7 is preferably mountable reversibly on the positioning plate 11 of the storage unit 4. In the embodiment shown, a plug-in dovetail connection connects the sample part magazine 7' to the positioning plate 11, which is vertically movable here. The sample part magazine 7' may thus be held on the handle 42 and lowered in the essentially vertical direction into the housing 5 and plugged onto the dovetail 43 of the positioning plate 11. Because the two magazines 7',9' are situated vertically one above another here, the test part magazine 9' permanently screwed onto the positioning plate 11 preferably represents the lower stop for the sample part magazine 7' inserted into the dovetail 43.

The depositories 6 in the sample part magazine 7' and/or in the test part magazine 9' are implemented for receiving slides which essentially have the dimensions of a standard slide for light microscopy. These depositories 6 are preferably separated from one another by bearing webs 12, so that these slides each rest on two bearing webs 12 extending essentially over the entire length of the slides 8,10.

Figure 2:
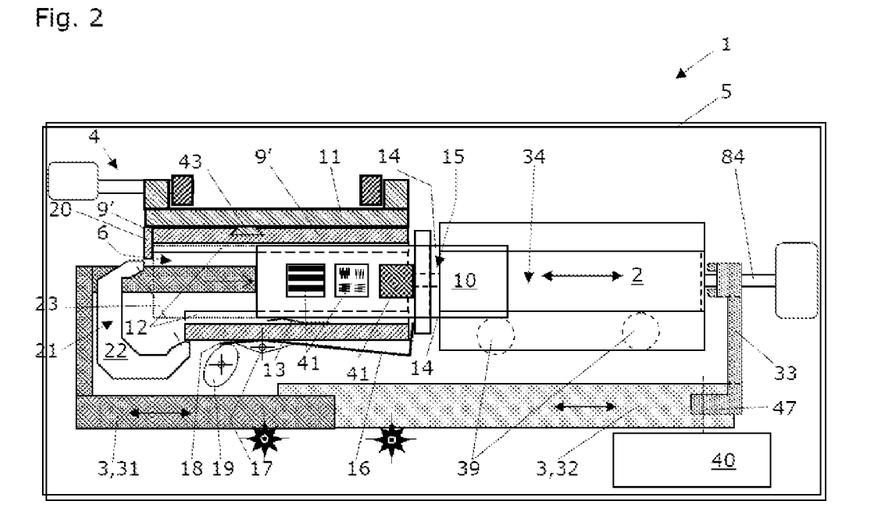
FIG. 2 shows a horizontal section through the slide magazines and a top view of the object table placed in front of them during transfer of a test slide from the test object magazine onto the object table.

FIG. 2 shows a horizontal partial section through the slide magazine shown in FIG. 1 and a top view of the object table placed in front of it during transfer of a test slide from the test object magazine onto the object table. The test part magazine 9' shown here comprises an open insertion side 15, which may be covered in its width at least partially by an individual foldaway flap 16 extending essentially over the entire stack height of the magazine 9'. This flap 16 is folded away here, so that the test slide shown may be pushed out of the insertion side 15 of the test part magazine 9', without being obstructed by the foldaway flap 16.

In the case of the test part magazine 9', this foldaway flap 16 forms a part of the lock which allows a test slide 10 stored in the test part 9 not to be manually accessible to an operator in the operating state of the laser scanner device 1. In the case of the sample part magazine 7', this foldaway flap 16 allows, in its folded-in state, the handling (for example, the pivoting or tilting) of the magazine 7' filled with at least one sample slide 8, without this object slide falling out being a concern. Preferably, both the sample part magazine 7' and also the test part magazine 9', but at least the sample part magazine 7' has a blocking plate 20 extending essentially over the entire stacking height on its side opposite to the insertion side 15, which covers a part of the width of this side. This blocking plate 20 in particular prevents object slides from falling out on the other side when the sample part magazine 7' is handled.

Individual foldaway flaps 16 are preferably fastened so they are rotatable on an axis 17 situated laterally of the magazines 7',9' for each magazine 7',9'. These individual foldaway flaps 16 each comprise an angle plate 18, which preferably extends essentially over the entire stack height of the magazines 7',9'. These foldaway flaps 16 are preferably pressed using a rotatable eccentric roller 19 driven by a motor against the particular magazine 7',9' to expose the insertion side 15 of one of the magazines 7',9'. Variants which are not shown comprise the movement of the foldaway flaps 16 using a lever, a tappet, or a slider.

In order that the slides 8,10 are seated in the magazines 7',9' essentially without play, each of these depositories 6 preferably comprises a contact pressure spring 13, which elastically impinges a longitudinal edge 14 of an inserted slide. In addition, the particular opposing longitudinal edge 14 of the slide 8,10 is held by the spring force in a location defined by the corresponding magazine 7',9', which is suitable for defining the origin of a coordinate system. The sample table 2 is also preferably equipped with movable contact pressure parts 39 in the form of rolls (cf. FIG. 2), which also fix the same longitudinal edge 14 in a defined location, because of which the same origin of the coordinate system also applies on the sample table 2.

At a corner opposite to the insertion side 15, at least the sample part magazine 7' preferably comprises a check opening 21 extending essentially over the entire stack height for establishing the presence or absence of a slide in a specific depository 6. The presence or absence of a slide 8,10 in a specific depository 6 may be established using various methods and devices. Thus, for example, (cf. FIG. 2) an essentially horizontally extending light beam 23 or a light barrier of a check device 22 may be directed diagonally through the magazines 7',9', if the check opening 21 is transparent to this light beam 23. The deflection, scattering, or attenuation of the light beam 23 by a slide 8,10 present in a depository 6 may be established easily using a light-sensitive sensor. While a check opening 21 in the form of a "cut-off corner" is shown in FIG. 2, the light beam 23 may also be transmitted through the insertion side 15 into the magazines 7',9' and be incident on a sensor on the opposing side, which is not cut off; a diagonal orientation in relation to the transport direction of the slides 8,10 and/or the attachment of a deflection mirror (neither shown) also allows detection of the slides in their magazines even with proximal sample table 2.

Further variants for establishing the presence or absence of a slide in a specific depository 6 of one of the two magazines 7',9' are based on capacitive proximity detection, for example.

The transport device 3 of the laser scanner device 1 preferably comprises an unloading slider 31, which is implemented to engage essentially parallel to the sample plane 49 through the side opposite to the insertion side 15 of the magazines 7',9' and to transport a sample slide 8 or a test slide 10 from its depository 6 and out of the insertion side 15 to the sample table 2. This transport device 3 preferably also comprises a loading slider 32, which is implemented for transporting a sample slide 8 or a test slide 10 from the sample table 2 and through the insertion side 15 into a depository 6 in one of the magazines 7',9'. Especially preferably, loading slider 32 comprises a pivotable flap 33, which may be pivoted up and thus moved away over the slide 8,10 inserted in the sample table 2 without this flap 33, which is tiltable around an axis 47, contacting the slide. This flap may thus be moved over the slide 8,10 and lowered behind it, after which the slide may be engaged by the flap 33 and pulled out of the sample table 2.

Figure 3A:
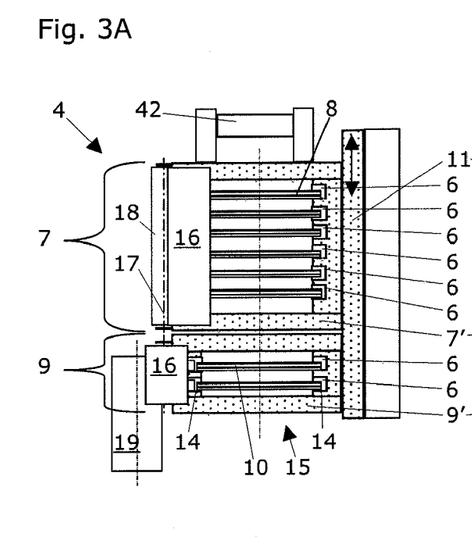

FIG. 3 shows vertical views of the slide magazines having open test object magazine. FIG. 3A shows the insertion side of the two slide magazines in a frontal view seen from the object table. The vertically movable positioning plate 11 is visible on the right side and its mobility is marked by a double arrow. The sample part 7 is situated exactly above the test part 9, the sample part magazine 7', having eight sample slides 8 resting in the depositories 6 here, being fastened axially above the test part magazine 9' having two test slides 10 here. The foldaway flap 16 of the sample part magazine 7' is closed, while the foldaway flap 16 of the test part magazine 9' is open and exposes essentially the entire width of the insertion side of the test part magazine 9'. Folding away of the foldaway flap 16 of the test part magazine 9' is caused here by the eccentric roller 19, which presses on the angle plate 18 of this flap. The eccentric roller 19 is preferably situated at least close to the sample plane 49 defined by the sample table 2, so that the correct flap 16 is always folded away in spite of the displacement of the storage unit 4 in height. The contact pressure springs of the test part magazine 9' may be seen well, as they press elastically on one lateral edge 14 of the test slides 10.

Figure 3B:
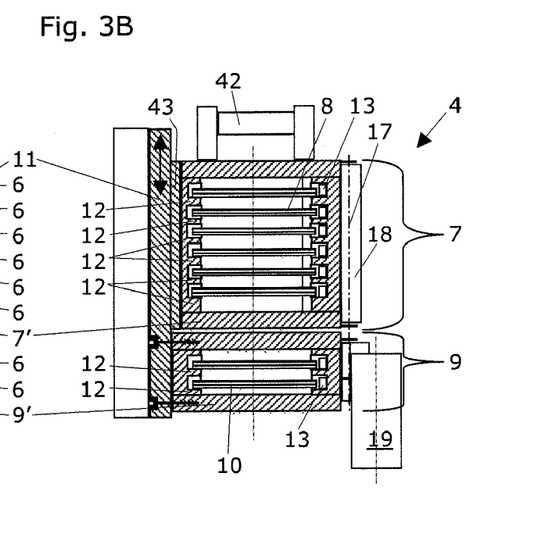

FIG. 3B shows the two slide magazines in vertical section looking toward the object table. The vertically movable positioning plate 11 is visible on the left side and its mobility is marked by a double arrow. The sample part magazine 7' is pushed over the dovetail 43 of the positioning plate 11 and is held in a constant position on the positioning plate 11 by the test part magazine 9' here. The test part magazine 9' is screwed permanently onto the positioning plate 11 here. The contact pressure springs 13 of the sample part magazine 7' and the test part magazine 9' may be seen well on the right side of the slide stack.

Figure 4:
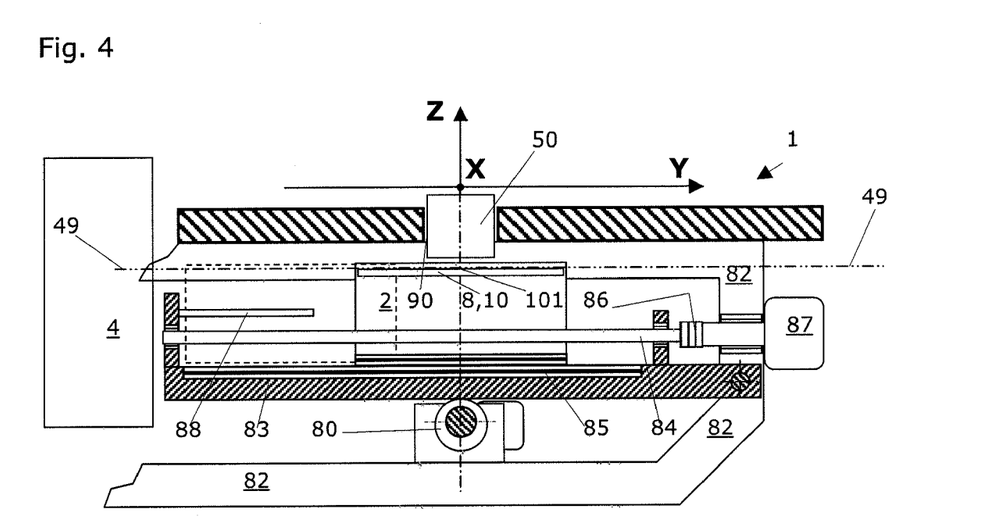
FIG. 4 shows a vertical section through the object table and its height adjustment and longitudinal inclination device.

FIG. 4 shows a vertical partial section through the object table and its height adjustment and longitudinal inclination device. The sample plane 49 defined by the sample table 2 is adjustable essentially in the Z direction (the vertical direction here), in that the sample table, which is linearly fastened and linearly displaceable on a suspension 83, rests together with this suspension 83 on an eccentric 80 driven by a motor and is fastened on one side on a frame 82 so it is pivotable. If the eccentric 80 is rotated somewhat, the suspension 83 rises or sinks accordingly with the sample table 2. The plane 49 of the sample table 2 may be brought into correspondence with the plane of a depository 6 in the sample part magazine 7' or in the test part magazine 9' of the storage unit 4 using this movement, so that a linear transfer may occur between one of these magazines 7', 9' and the sample table. The corresponding magazine is preferably provided in the Z direction by a displacement of the movable positioning plate 11, so that only any fine adjustment must be performed using the eccentric 80 of the sample table suspension 83.

For the purpose of such a slide transfer, the sample table 2 preferably approaches as close as possible to the storage unit 4 in the essentially horizontal Y direction. During the approach of the sample table 2 to the storage unit 4, a recessed mandrel 88 presses into the sample table 2 and thus lowers a support of the receptacle 34 of the sample table 2 to receive a slide. The sample table 2 is thus provided for receiving a slide 8,10. This approach preferably occurs using a spindle drive 84 mounted on the suspension 83 and along a linear guide 85. The spindle drive 84 is connected via a flexible coupling 86 to the motor 87, so that an exact linear guide of the sample table 2 in essentially the Y direction may occur even if the sample plane 49 encloses a slight angle of inclination to the horizontal. The goal of the adjustability of the sample table 2 using the eccentric 80 is primarily the orientation of the sample plane 49 to a focal line 101, which is defined by a scanner head 50 of the laser scanner device 1 oscillating in the X direction (perpendicular to the plane of the drawing here). This scanner head 50 moves very rapidly in the X direction and on the top side of a partition plate 99. This partition plate has a scanning opening 90. The scanner head 50 is preferably lowered into this scanning opening 90 so that the light beams emitted therefrom are incident on the sample at a slight distance, and the scanner head 50 may absorb the fluorescence emission coming from the sample as effectively as possible and relay it to a detector 61 or to multiple detectors 61.

Figure 5:
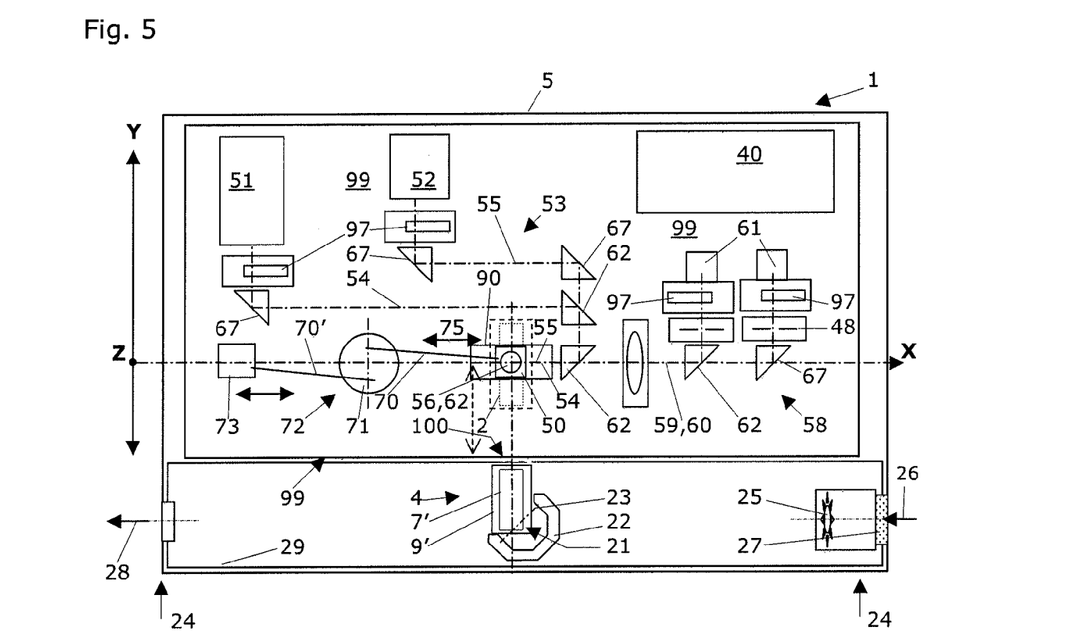
FIG. 5 shows a horizontal partial section through a laser scanner device having essential optical elements, a scanner unit having scanner head, and an object table having slide magazines.

FIG. 5 shows a horizontal partial section through a laser scanner device 1 having essential optical elements of a first optical system 53 for providing excitation light and a second optical system 58 for detecting the triggered fluorescence emission of the samples, having a scanner apparatus 72, having an object table 2, and having a storage unit 4. All essential optical elements and the scanner apparatus 72 are preferably situated on a shared partition plate 99 and the sample table 2 preferably is situated below this partition plate 99 (cf. FIG. 4).

The essential optical elements of the first optical system 53 are situated in a housing 5 and comprise at least one first laser 51 and optionally one second laser 52, filter wheels 97 for the laser beams 54,55 originating from the laser(s) 51,52, and a number of dichroic mirrors 62 and simple mirrors 67 for deflecting the laser beams 54,55 from the lasers 51,52 in a direction parallel to the X direction.

The essential optical elements of the second optical system 58 are situated in the same housing 5 and comprise one or more detectors 61, filter wheels 97 situated in front of them and apertures 48 for the emission beam bundles 59,60 originating from the samples, as well as a number of dichroic mirrors 62 and simple mirrors 67 for deflecting the emission beam bundles 59,60 from a direction parallel to the X direction in the direction of the detectors 61.

The scanner apparatus 72 comprises a drive 71, the scanner head 50, and preferably a counter oscillator 73 having a mass equal or at least equivalent to the scanner head 50 for momentum compensation. Scanner head and counter oscillator are connected to the drive 71 using connecting rods 70,70' and are each fastened to a precise linear guide (not shown). The scanner head 50 is brought into a rapid back-and-forth movement in a movement direction (cf. solid double arrows) by the drive 71, which simultaneously defines the scanning axis 75. The counter oscillator 73 always executes an opposing movement, because of which the partition plate 99 and thus the entire laser scanner device 1 are held steady in spite of the preferred high scanning velocity of the scanner head 50. The scanning axis 75 is parallel to the X axis or is precisely coincident therewith. The scanner head 50 comprises an optical deflection element 56, which is implemented as a dichroic mirror 62, for example. This deflection element 56 may be implemented as a solid mirror, prism, pentaprism, pentamirror configuration, or as a combination of the elements listed here. This deflection element 56 deflects the laser beams 54,55 of the first optical element 53 onto the samples on the sample table 2 on one hand and the emission beam bundles 59,60 emitted from the samples in the direction of the second optical system 58 on the other hand.

Perpendicular to the X axis and scanning axis 75, the movement direction of the sample table 2 situated below the partition plate 99 runs in the direction of the Y axis. The storage unit 4 having the sample slides 8 stored in a sample part magazine 7' and the test slides 10 stored in a test part magazine 9' is preferably situated in an area outside the partition plate 99. The presence of a slide 8,10 in a specific depository 6 of these magazines 7',9' is preferably monitored using a checking device 22. This checking device preferably comprises a light beam 23, which penetrates a check opening 21 for these checking purposes.

The laser scanner device 1 preferably has a ventilation apparatus 24 having a ventilator 25, an air inlet 26 having an activated carbon filter 27, and an air outlet 28, to reduce the exposure of the fluorescent pigments on or in the samples stored in the sample part magazine 7' to ozone. The ventilation apparatus 24 especially preferably comprises an additional housing 29, which essentially encloses the sample part 7 having the sample slides 8. This additional housing 29 is preferably situated inside the housing 5 of the laser scanner device 1 and implemented as an essentially closed area which may be pivoted away. It is especially preferable for the ventilation apparatus 24 to be housed in this additional device 29 and be independent of the ventilation of the laser scanner device 1.

A service technician, for example, may open this additional housing 29 and, if necessary, insert or replace one or more test slides in the otherwise inaccessible test part magazine 9'. This additional housing 29 is preferably implemented as pivotable away from the partition plate 99 and has a loading opening 100, through which a slide 8,10 may be transported onto the sample table 2 or into a magazine 7',9'. The sample part 7 is preferably situated axially above the test part 9 of the storage unit 4 and is pivoted away together with the additional housing 29 or at least together with a part of this additional housing (which is thus opened for the service technician).

It is especially preferable for a service technician to insert one or more test slides 10 individually into a sample part magazine 7' and to insert this sample part magazine 7' on the proper pathways into the laser scanner device 1. Correspondingly programmed firmware in the controller 40 of the laser scanner device 1 is then preferably activated by input of a personal identification number (PIN) of the service technician and/or by input of a code for the service personnel. The firmware thus activated makes the controller 40 of the laser scanner device 1 capable of controlling the automatic transport of each of these test slides 10 out of the sample part magazine 7' onto the sample table 2 and further into a depository 6 of the test part magazine 9'. According to this especially preferred method, any manual intervention into the test part magazine 9' is made impossible. The service technician may only retrieve the test slide 10, which is preferably enclosed in the additional housing 29, in special emergency cases using suitable tools. The controller 40 of the laser scanner device 1 according to the invention is preferably implemented for controlling an automated internal instrument check executed on the basis of test slides 10.

The sample table 2 is preferably implemented to move driven by a motor up to directly in front of the storage unit 4 and its location and movement are controlled by the controller 40. This is also true for the positioning plate 11 of the storage unit 4 for selecting the slide 8,10 to be studied and for the rotatable eccentric roller 19 for pivoting away the flap 16. In addition, it is preferable for the unloading slider 31 to transport an object slide 8,10 to the sample table 2 for the automated selection and provision of a sample slide 8 or test slide 10 on the sample table 2 to be implemented as driven by a motor and for its location and movement to be controlled by the controller 40. This is also true for the loading slider 32 for transporting a slide 8,10 to the storage unit 4 when it is placed back in a depository 6 of the sample part magazine 7' or the test part magazine 9'.

Figure 6:
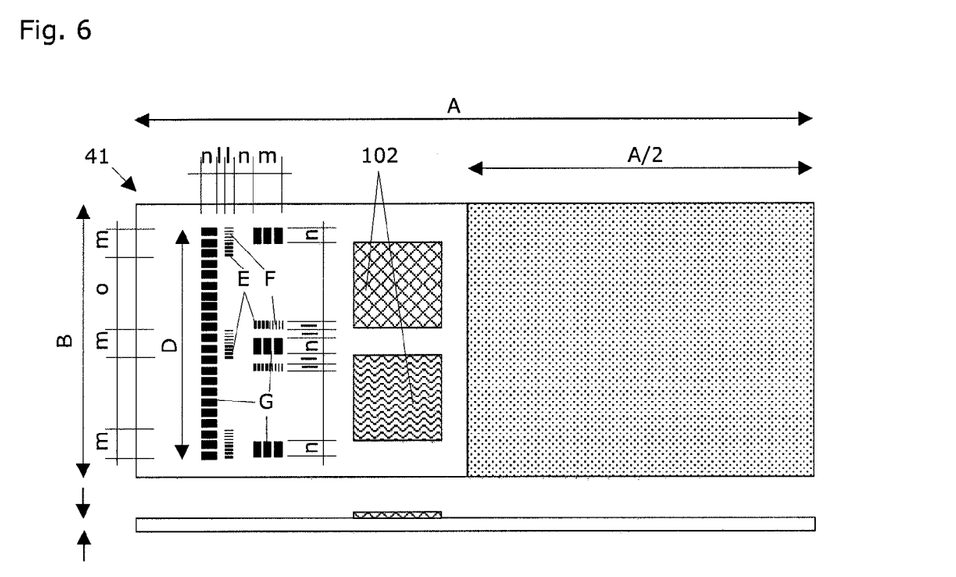
FIG. 6 shows a test slide which has the format of a standard slide for light microscopy and which comprises exclusively essentially light-stable test structures.

FIG. 6 shows a test slide 10 which has the format of a standard slide for light microscopy and exclusively comprises essentially light-stable test structures 41. "Essentially light-stable" refers to a test structure if this does not suffer any measurable damage during normal use, i.e., upon the radiation load typically occurring during testing methods. A minute-long or even hour-long irradiation of a test slide 10 using a laser beam 54,55 is not referred to as "normal use".

Following Table 1 gives an overview of the most typical glass slides for light microscopy:

| Type | Inch: 1 × 3 inches | Metric: 25 × 75 mm |
|---|---|---|
| Dimensions: | | |
| Length × width (Tolerances) | 76.2 mm × 25.4 mm (±0.5 mm) | 76 mm × 25 mm (±0.5 mm) |
| Thickness: | | |
| "standard" | 1.02 mm (±0.05 mm) | 1.02 mm (±0.05 mm) |
| "thick" | 1.2 mm (±0.1 mm) | |

-continued

| Type | Inch: 1 × 3 inches | Metric: 25 × 75 mm |
|---|---|---|
| Handling: | | |
| Corners | sharp, milled | sharp, milled |
| Edges | sharp, milled | sharp, milled |
| Surfaces | blank, sandblasted, on one or both sides | blank, sandblasted, on one or both sides |

The exemplary test slide 10 shown in FIG. 6 has a surface having a length A of 75 mm, a width B of 25 mm, and a thickness C of 1 mm. One half of the surface A/2 is matted (for example, using grinding). The other half preferably has a line pattern having a width D of 20 mm.

This line pattern preferably comprises a vapor-deposited chromium layer prepared using a mask. The capital letters E, F, G identify a specific number of line pairs per millimeter (lp/mm) and the lower case letters l, m, n, o identify specific quantities as follows:

E=50 lp/mm; F=100 lp/mm; G=10 lp/mm;

l=0.5 mm; m=2 mm; n=1 mm; o=7 mm.

All of these test structures 41 are preferably exclusively essentially light-stable and non-fluorescent.

The laser scanner device 1 according to the invention is designed for imaging and measuring two-dimensional objects. Correspondingly, a sensitivity calibration must be valid precisely for these "flat" objects. Two-dimensional fluorescent samples which are both light-stable and also chemically resistant over long periods of time may be produced only with difficulty or not at all, however.

In contrast, objects which have a three-dimensional extension may be measured. However, because the intensities measured on such three-dimensional objects are strongly dependent on the depth of field of the laser scanner device and the particular positioning in the focus (i.e., in the Z direction), such three-dimensional objects are not directly suitable for calibrating signal intensity or sensitivity. However, materials 102 exist as so-called "bulk material", such as fluorescent pigments embedded in plastic or doped glasses, which are light-stable and chemically resistant as extensively as possible.

The orientation of the sample table 2 and the storage unit of the laser scanner device 1 in space actually is arbitrary. This is also true for the scanner apparatus 72, which is well-balanced and/or momentum-compensated using counter oscillator 73. The sample plane 49 of the sample table 2 may also be situated essentially horizontal but hanging overhead. However, a vertical configuration of the sample table as shown in FIGS. 1 and 2 or 4 and 5 is preferred.

Identical features or elements of the laser scanner device 1 according to the invention are each provided with identical reference numerals, although these elements are not described in detail in all cases.

In addition, a method according to the invention for operating such a laser scanner device 1 for imaging and/or measuring fluorescent samples located on slides and treated using fluorescent pigments is disclosed. This method is characterized in that the test part 9 is implemented as a test part magazine 9', separate from the sample part 7 and permanently connected to the laser scanner device 1, for one or more test slides 10, at least one depository 6 for test slides 10 for performing an instrument check being provided, which is not manually accessible to an operator in the operating state of the laser scanner device 1.

An instrument check which is selected from a group which comprises the performance of intensity and sensitivity tests, crosstalk, resolution, and dynamic measurements, laser noise and intensity measurements, and filter blocking and filter transmission checks as well as the checking of the adjustment of optical components, the geometric image parameters, and the image orientation, is especially preferred. Geometric image parameters are, for example, the imaging scale and the establishment and parameterization of distortions. Superpositions of two or more excitation channels and/or detection channels may also be checked. Furthermore, the laser scanner device 1 is capable of checking the autofocus function.

A sensitivity check is preferably performed without fluorescent substance, using at least one test slide 10 which at least approximately has the format of a standard slide for light microscopy and which exclusively comprises essentially light-stable test structures 41.

Alternatively or additionally to the sensitivity check on essentially two-dimensional test structures 41 without fluorescent substance cited above, an intensity measurement may also be performed on three-dimensional fluorescent test structures:

Instead of a normal scan and/or a normally scanned field in the XY direction and thus parallel to the sample plane 49, a scan is performed in the XZ direction (Z profile), in that a field is scanned which is at least essentially perpendicular to the sample plane 49. The directly measured Z profile represents the measured intensity as a function of the Z coordinate (I=I(Z)). Instead of this Z profile, the first derivative of the corresponding intensities (dI=dI(z)/dz) is preferably calculated, because of which a two-dimensional intensity distribution is again provided. The maximum of the first derivative is thus a measure of the intensity measured by the laser scanner device 1 on the surface of the sample.

The materials 102 suitable for this calibration method may be situated together with the vapor-deposited line pattern on the same test slide 10 or on a separate test slide. These flat, three-dimensional materials 102 preferably have an extension parallel to the sample plane 49 of 2×2 mm to 10×10 mm and have a thickness of approximately 0.1 to 2 mm, preferably a thickness of approximately 1 mm (cf. FIG. 6).

LIST OF REFERENCE NUMERALS 1 laser scanner device
2 sample table
3 transport device
4 storage unit
5 housing
6 depository
7 sample part
7' sample part magazine
8 sample slide
9 test part
9' test part magazine
10 test slide
11 movable positioning plate
12 bearing webs
13 contact pressure spring
14 longitudinal edge of slide
15 insertion side
16 foldaway flap
17 axis
18 angle plate
19 eccentric roller
20 blocking plate
21 check opening 22 checking device
23 light beam
24 ventilation apparatus
25 ventilator
26 air inlet
27 activated carbon filter
28 air outlet
29 additional housing
31 unloading slider
32 loading slider
33 pivotable flap
34 receptacle
39 movable contact pressure parts
40 controller
41 test structures
42 handle
43 dovetail
47 tilt axis of 33
48 aperture
49 plane, sample plane
50 scanner head
51 first laser
52 second laser
53 first optical system
54 first laser beam
55 second laser beam
56 optical deflection element
58 second optical element
59 emission beam bundle
60 emission beam bundle
61 detector
62 dichroic mirror
67 simple mirror
70,70' connecting rod
71 drive
72 scanner apparatus
73 counter oscillator
75 movement direction, scanning axis
80 motorized eccentric
82 frame
83 suspension
84 spindle drive
85 linear guide
86 coupling
87 motor
88 recessed mandrel
90 scanning opening
97 filter wheel
99 partition plate
100 loading opening
101 focal line
102 flat materials

What is claimed is:

1. A laser scanner device (1) for imaging or measuring fluorescent samples located on slides and treated using fluorescent pigments, which comprises a sample table (2), defining a sample plane (49), and a motorized transport device (3) for moving a slide from a storage unit (4) to the sample table (2) and back, the storage unit (4) comprising one sample part (7) for sample slides (8) and one test part (9) for test slides (10), which each have at least one depository (6) and are each accessible during operation of the laser scanner device (1) to the transport device (3), wherein the test part (9) is implemented as separate from the sample part (7) and as a test part magazine (9') that is permanently connected to the laser scanner device (1) and that is for one or more test slides (10);

wherein the test part (9) is permanently connected to the positioning plate (11) of the storage unit (4), because of which a test slide (10) stored in the test part (9) is not manually accessible to an operator in the operating state of the laser scanner device(1);

wherein the sample part (7) is reversibly mounted on the positioning plate (11) of the storage unit (4); and wherein the positioning plate (11) is movable in relation to the sample table (2) of the laser scanner device (1).

2. The laser scanner device according to claim 1, wherein the sample part (7) is situated axially above the test part (9); and wherein the positioning plate (11) of the storage unit (4) is displaceable substantially perpendicularly in relation to the sample plane (49) of the sample table (2).

3. The laser scanner device according to claim 2, wherein the sample table (2) is implemented as movable up to immediately in front of the storage unit (4) for the transfer of sample slides (8) or test slides (10); and wherein the positioning plate (11) of the storage unit (4) is implemented to bring one of the sample slides (8) or test slides (10) stored in the storage unit (4) to the level of the sample plane (49) defined by the sample table (2), the sample slide (8) or the test slide (10) being thus provided for linear transport onto the sample table (2).

4. The laser scanner device according to claim 1, wherein the sample plane (49) of the sample table (2) is situated substantially horizontally.

5. A method for operating a laser scanner device for imaging or measuring fluorescent samples located on slides and treated using fluorescent pigments, the method comprising the steps of:

a) providing a laser scanner device (1) comprising:
a sample table (2) defining a sample plane (49), and
a motorized transport device (3) for moving a slide from a storage unit (4) to the sample table (2) and back, and the storage unit (4) comprising one sample part (7) for sample slides (8) and one test part (9) for test slides (10), each having at least one depository (6) and each being accessible during the operation of the laser scanner device (1) for the transport device (3), the test part (9) is implemented separately from the sample part (7) and as a test part magazine (9'), permanently connected to the laser scanner device (1), for one or more test slides (10);

b) providing at least one depository (6) for test slides (10);

c) providing a positioning plate (11) of the storage unit (4), the test part (9) being permanently connected to this positioning plate (11), a test slide (10) stored in the test part (9) being thus not manually accessible to an operator in the operating state of the laser scanner device (1);

d) reversibly mounting the sample part (7) on the positioning plate (11) of the storage unit (4); and e) moving the positioning plate (11) in relation to the sample table (2) of the laser scanner device (1).

6. The method according to claim 5, which comprises the following steps:

(a) one or more test slides (10) are individually inserted into a sample part magazine (7');

(b) this sample part magazine (7') is inserted into the laser scanner device (1);

(c) firmware in the controller (40) of the laser scanner device (1) is activated; and (d) the activated firmware makes the controller (40) of the laser scanner device (1) capable of controlling the automatic transport of each of these test slides (10) from the sample part magazine (7') onto the sample table (2) and further into a depository (6) of the test part magazine (9');
wherein by the movement of the positioning plate (11) of the storage unit (4), a test slide (10) stored in the storage unit (4) is brought to the level of the sample plane (49) defined by the sample table (2).

\* \* \* \* \*